United States Patent
Noda et al.

(10) Patent No.: US 7,387,124 B2
(45) Date of Patent: Jun. 17, 2008

(54) METHOD OF AND DEVICE FOR SNORE DETECTION

(75) Inventors: Satoshi Noda, Hirakata (JP); Takeshi Minamiura, Osaka (JP); Hidetaka Sakai, Katano (JP)

(73) Assignee: Sanyo Electric Co., Ltd., Osaka (JP)

( * ) Notice: Subject to any disclaimer, the term of this patent is extended or adjusted under 35 U.S.C. 154(b) by 18 days.

(21) Appl. No.: 11/074,742

(22) Filed: Mar. 9, 2005

(65) Prior Publication Data
US 2005/0211247 A1    Sep. 29, 2005

(30) Foreign Application Priority Data
Mar. 25, 2004  (JP)  ............... 2004-090380
Jun. 22, 2004  (JP)  ............... 2004-183732

(51) Int. Cl.
*A61M 16/00* (2006.01)
*A61B 5/08* (2006.01)

(52) U.S. Cl. .................. 128/204.23; 128/205.23; 600/532; 600/533; 600/534

(58) Field of Classification Search ......... 128/202.22, 128/204.23, 205.23, 200.24, 920; 600/483, 600/484, 529, 532–534, 538, 586
See application file for complete search history.

(56) References Cited

U.S. PATENT DOCUMENTS

| | | | | |
|---|---|---|---|---|
| 5,199,424 A | * | 4/1993 | Sullivan et al. | 128/204.18 |
| 5,259,373 A | * | 11/1993 | Gruenke et al. | 128/204.23 |
| 5,551,418 A | * | 9/1996 | Estes et al. | 128/204.23 |
| 5,671,733 A | * | 9/1997 | Raviv et al. | 128/630 |
| 5,921,942 A | * | 7/1999 | Remmers et al. | 600/529 |
| 5,953,713 A | * | 9/1999 | Behbehani et al. | 706/16 |
| 5,989,193 A | | 11/1999 | Sullivan | |
| 6,017,315 A | * | 1/2000 | Starr et al. | 600/538 |
| 7,150,718 B2 | * | 12/2006 | Okada et al. | 600/538 |
| 2006/0009704 A1 | * | 1/2006 | Okada et al. | 600/529 |

FOREIGN PATENT DOCUMENTS

| | | |
|---|---|---|
| JP | 07-184948 | 7/1996 |
| JP | 11-505146 | 5/1999 |
| WO | WO 96/36279 | 11/1996 |

OTHER PUBLICATIONS

Japanese Office Action issued in corresponding Japanese Patent Application No. 2004-183732, dated Jan. 31, 2007.

* cited by examiner

*Primary Examiner*—Justine R. Yu
*Assistant Examiner*—Shumaya Ali
(74) *Attorney, Agent, or Firm*—McDermott Will & Emery LLP

(57) ABSTRACT

The present invention provides a snore detection device comprising a pressure sensor for detecting vibration generated by the human body with respiration, a sound sensor for detecting sound generated by the human body with respiration, and a judging circuit for judging the occurrence of snoring based on output signals of the two sensors. The judging circuit detects a peak occurrence time in variations generated by the output signal of the pressure sensor and a peak occurrence time in variations generated by the output signal of the sound sensor, to judge whether snoring occurs based on the peak occurrence times, respectively, of vibration and sound.

1 Claim, 15 Drawing Sheets

METHOD OF AND DEVICE FOR SNORE DETECTION

BACKGROUND OF THE INVENTION

1. Field of the Invention

The present invention relates to a snore detection method and a snore detection device.

2. Description of Related Art

Detection of snoring during sleep makes it possible to diagnose one's health state or to prevent the occurrence of snoring. Already proposed are a snore detection device for judging whether snoring occurs based on vibration (pressure variations), generated by the human body with respiration, and another snore detection device for judging whether snoring occurs based on snoring sound (JP-A No. 184948/1995).

According to FIG. 13, however, an investigation of the phase relationship between pressure data variations obtained by measuring vibration generated by the human body with respiration and sound data variations obtained by measuring snoring sound reveals that there exist following cases: the time at which the peak P1 of the pressure data appears corresponds to the time at which the peak P2 of the sound data appears, as seen in FIG. 13(a); the time at which the peak P2 of the sound data appears falls behind the time at which the peak P1 of the pressure data appears, as seen in FIG. 13(b); the time at which the peak P2 of the sound data appears is earlier than the time at which the peak P1 of the pressure data appears, as seen in FIG. 13(c). This is because the magnitude of snoring sound is varied in accordance with speed of respiration air flow or airway state while the magnitude of pressure data is varied in accordance with a posture of the sleeping human body. Accordingly the appearance of the peak of the sound data is not always in synchronism with that of the peak of the pressure data.

Thus a snore detection device for judging whether snoring occurs based only on the variations of the pressure data, and a snore detection device for judging whether snoring occurs based only on the variations of the sound data are low in accuracy, and are likely to erroneously judge vibration or sound generated by causes other than snoring as the occurrence of snoring, as the case may be.

SUMMARY OF THE INVENTION

An object of the present invention is to provide a method of and a device for snore detection with higher detection accuracy than conventionally.

The present invention provides a snore detection method of detecting waveforms, respectively, of vibration and sound generated by the human body with respiration to judge occurrence of snoring based on synchronous state of the vibration waveform and the sound waveform.

The present invention provides a snore detection device comprising a pressure sensor 2 for detecting vibration generated by the human body with respiration, a sound sensor 3 for detecting sound generated by the human body with respiration, and a judging circuit for judging whether snoring occurs based on output signals from the two sensors 2, 3. The judging circuit comprises peak detection means for detecting a peak occurrence time in variations generated by the output signal of the pressure sensor 2 and a peak occurrence time in variations generated by the output signal of the sound sensor 3, and judging means for judging whether snoring occurs based on the peak occurrence times, respectively, of vibration and sound detected by the peak detection means.

Stated specifically, when the difference between the peak occurrence times, respectively, of a vibration waveform and a sound waveform obtained continuously with time is smaller than a predetermined set value, the occurrence of snoring is judged. Alternatively, when the difference between an interval of the peak occurrence times of the vibration waveform and an interval of the peak occurrence times of the sound waveform is smaller than a predetermined set value, the occurrence of snoring is judged. Further alternatively, when the difference between the peak occurrence times, respectively, of the vibration waveform and the sound waveform obtained continuously with time is smaller than a predetermined set value, and the difference between an interval of the peak occurrence times of the vibration waveform and an interval of the peak occurrence times of the sound waveform is smaller than a predetermined set value, the occurrence of snoring is judged.

Furthermore, the present invention provides a snore detection device comprising a pillow 10 for supporting a head of the human body, a pressure sensor 2 for detecting vibration generated by the human body with respiration, a sound sensor 3 for detecting sound generated by the human body with respiration, and a judging circuit for judging whether snoring occurs based on output signals of the two sensors 2, 3. The sound sensor 3 is installed on a surface of or inside the pillow 10, between a mat contact surface on which the pillow 10 is in contact with a mat surface to be provided with the pillow 10 thereon and a head contact surface on which the pillow 10 is in contact with the head, and approximately beneath the head or a cervix of the human body.

Still furthermore, the snore detection device of the present invention comprises a mat 1 on which the human body is placed, a pressure sensor 2 for detecting vibration generated by the human body with respiration, a sound sensor 3 for detecting sound generated by the human body with respiration, and a judging circuit for judging whether snoring occurs based on output signals of the two sensors 2, 3. The sound sensor 3 is installed on a surface of or inside the mat 1, and approximately beneath a head or a cervix of the human body.

With the snore detection method and the snore detection device of embodying the present invention, the occurrence of snoring is judged in accordance with synchronous state of the vibration waveform and the sound waveform obtained with respiration based on two data of the two waveforms, whereby detection accuracy is higher than with the conventional method wherein the occurrence of snoring is judged based only on one of the vibration waveform and the sound waveform.

As described above, the snore detection method and the snore detection device of the present invention allow snore detection with higher accuracy than conventionally.

DETAILED DESCRIPTION OF THE INVENTION

With reference to the drawings, an embodiment of the present invention will be described below in detail. A snore detection device embodying the present invention comprises a pressure sensor 2 for detecting vibration generated by the human body sleeping on a mat 1 with respiration and a sound sensor 3 for detecting sound generated by the human body with respiration, as seen in FIG. 1.

Figure 2:
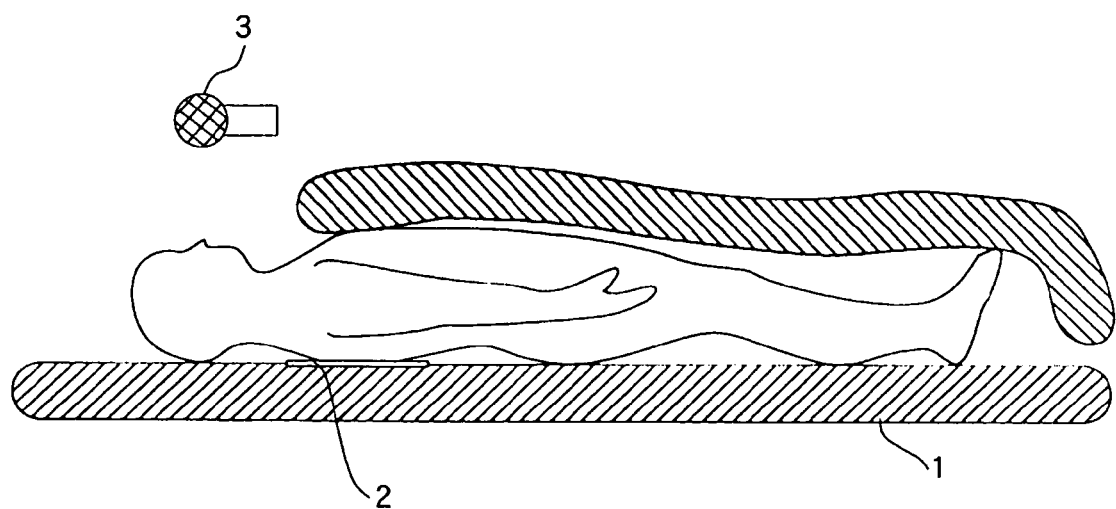
FIG. 2 is a diagram illustrating an arrangement of a pressure sensor and a sound sensor.
Figure 3:
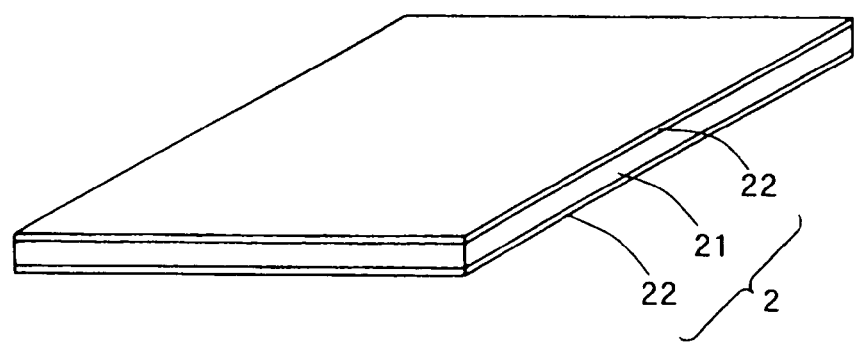
FIG. 3 is a perspective view showing a construction of the pressure sensor.

The pressure sensor 2 comprises, for example, a pair of conductive members 22, 22 each in the form of a sheet, and an elastic dielectric 21 in the form of a sheet which is sandwiched between the conductive members 22, 22, as seen in FIG. 3. The pressure sensor 2 detects pressure variations in response to variations in capacitance between the conductive members 22, 22. The pressure sensor 2 is installed under the human body lying face up on the mat 1, as seen in FIG. 2. Usable as the pressure sensor 2 are various known pressure sensors such as a strain gauge, exhalation band, airflow sensor, etc. The sound sensor 3 is installed above the human body sleeping face up on the mat 1, as seen in FIG. 2. Usable as the sound sensor 3 are various known sound sensors such as a condenser microphone, a dynamic microphone, etc.

Figure 1:
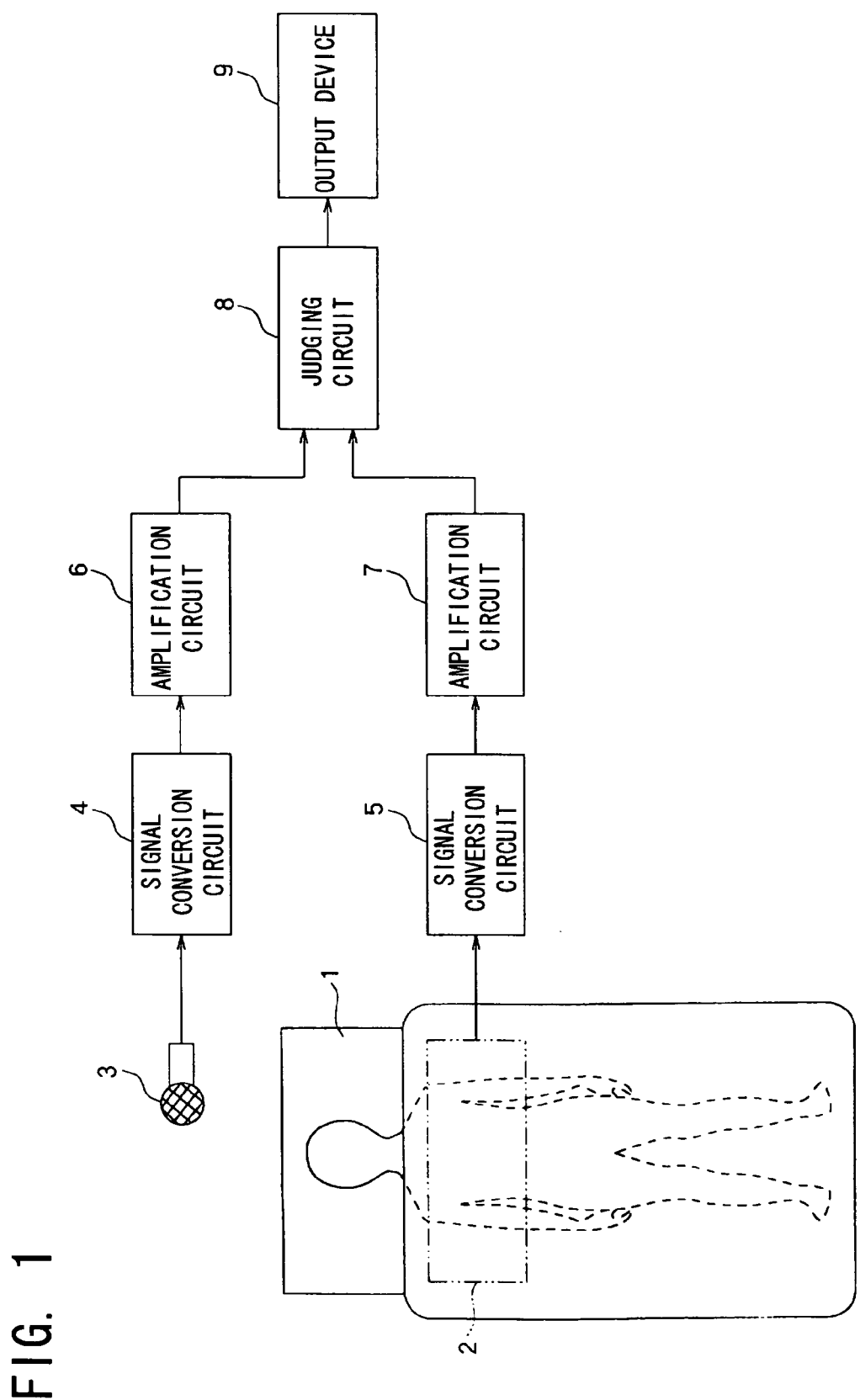
FIG. 1 is a block diagram showing a construction of a snore detection device according to the present invention.

With reference to FIG. 1, the pressure sensor 2 and the sound sensor 3 are each connected to a judging circuit 8 comprising a microcomputer via signal conversion circuits 4, 5 for noise elimination and feature extraction of signals and amplification circuits 6, 7. Judging results obtained by the judging circuit 8 are fed to an output device 9 such as a display, etc.

The signal conversion circuits 4, 5 eliminate the noise and extract the feature of signals, as described above, by giving a rectifying process by a band-pass filter and a moving average process by a low-pass filter to output signals from each of the pressure sensor 2 and the sound sensor 3.

The judging circuit 8 detects a peak occurrence time in variations generated by the output signals of the pressure sensor 2 and a peak occurrence time in variations generated by the output signals of the sound sensor 3, to judge whether snoring occurs in response to the peak occurrence time of the pressure and the peak occurrence time of the sound. Incidentally in the case where a posture and sleeping state of the human body is controlled in accordance with the judging result, the output from the judging circuit 8 is fed to a control circuit (not shown) for controlling the posture and sleeping state.

Figure 4:
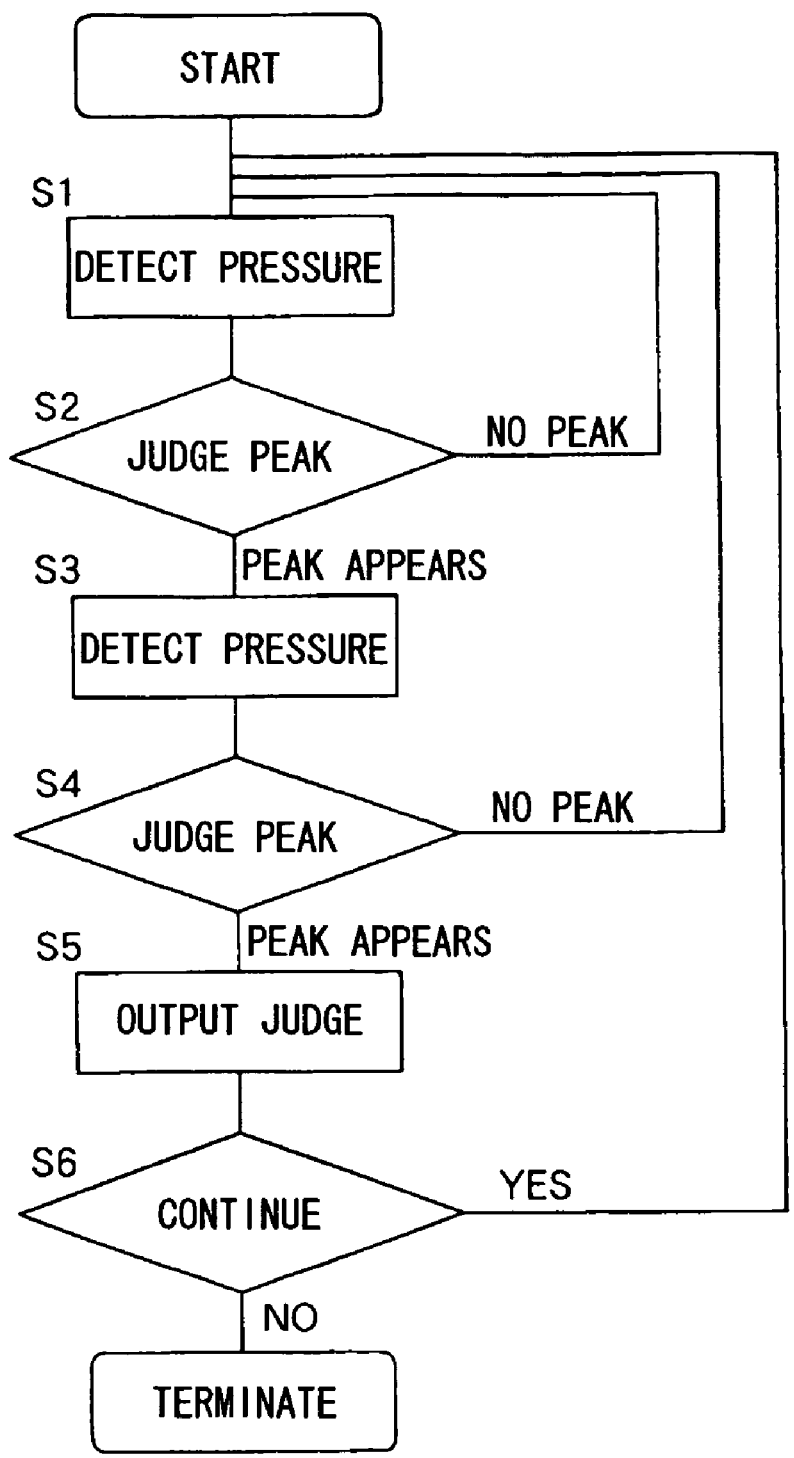
FIG. 4 is a flowchart showing a procedure of detecting snoring according to the present invention.

FIG. 4 shows a procedure of judging the occurrence of snoring to be performed by the judging circuit 8. First in step S1 variations of pressure are detected. In step S2, an inquiry is made as to whether the peak appears in the variations. When the inquiry is answered in the affirmative, step S3 follows to detect variations of sound. In step S4 an inquiry is made as to whether the peak appears in the variation. If the answer is affirmative, step S5 follows to judge whether snoring occurs based on a peak occurrence time of pressure and a peak occurrence time of sound to output the result. Thereafter in step S6, an inquiry is made as to whether checking the next peak is further to be continued. If the answer is negative, a series of procedure is terminated.

Figure 5:
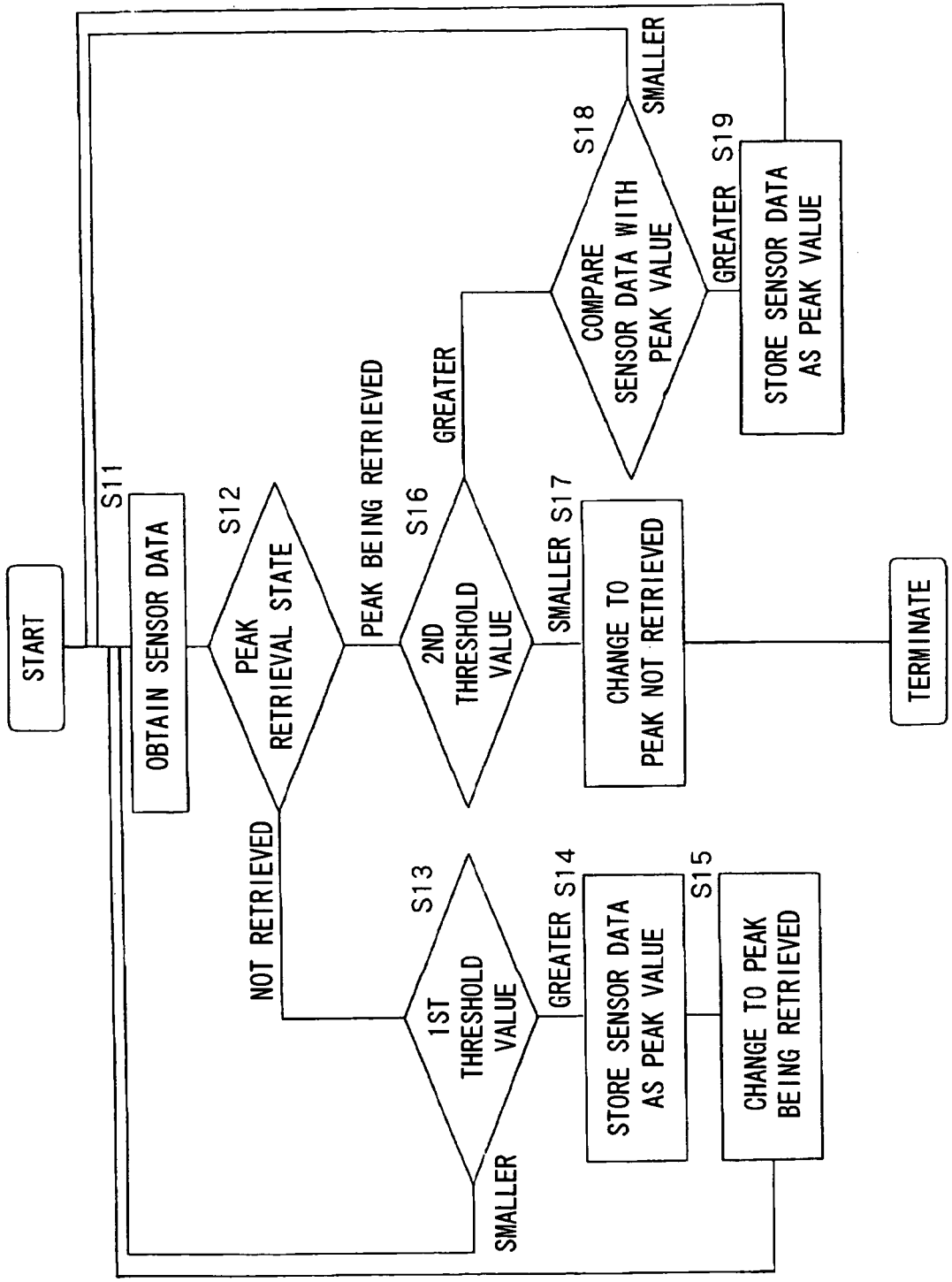
FIG. 5 is a flowchart showing a procedure of detecting the peak.

FIG. 5 shows a specific procedure of checking the peak in the aforementioned step S2 and step S4. First in step S11 sensor data (pressure data or sound data) is obtained from the aforementioned pressure sensor or sound sensor. In step S12 an inquiry is made as to whether the circuit is in a state of peak retrieval. If the peak is not retrieved, step S13 follows to inquire whether the sensor data is greater than a first threshold value. If the sensor data is found to be smaller than the first threshold value, step S11 follows again to repeat the same inquiry. When the sensor data is found to be greater than the first threshold value, step S14 follows to store the sensor data as a peak value. Further in step S15 the circuit changes the state of peak retrieval to a state of peak being retrieved, followed by step S11 again. Incidentally, in a waveform of varying measurement of pressure and sound as seen in FIG. 6, the first threshold value is set at a suitable value H through which the measurement is to pass while the measurement is increased for a period of the peak occurrence.

Accordingly the peak is found to be being retrieved in step S12 in FIG. 5, followed by step S16 wherein an inquiry is made as to whether the sensor data is smaller than a second threshold value. When the sensor data is found to be greater than the second threshold value, step S18 follows to compare the sensor data with the peak value. When the sensor data is greater than the peak value, step S19 follows to store the sensor data as a peak value, and step S11 thereafter follows again. When the sensor data is smaller than the peak value, step S19 is skipped and step S11 follows again. Incidentally, in a waveform of varying measurement of vibration or sound as seen in FIG. 6, the second threshold value is set at a suitable value L (L<H) through which the measurement is to pass while the measurement is decreased for a period of the peak occurrence.

Thereafter when the sensor data is to be found smaller than the second threshold value in step S16 in FIG. 5, step S17 follows to change the state of peak retrieval to a state of peak not retrieved, terminating the procedure.

Figure 6:
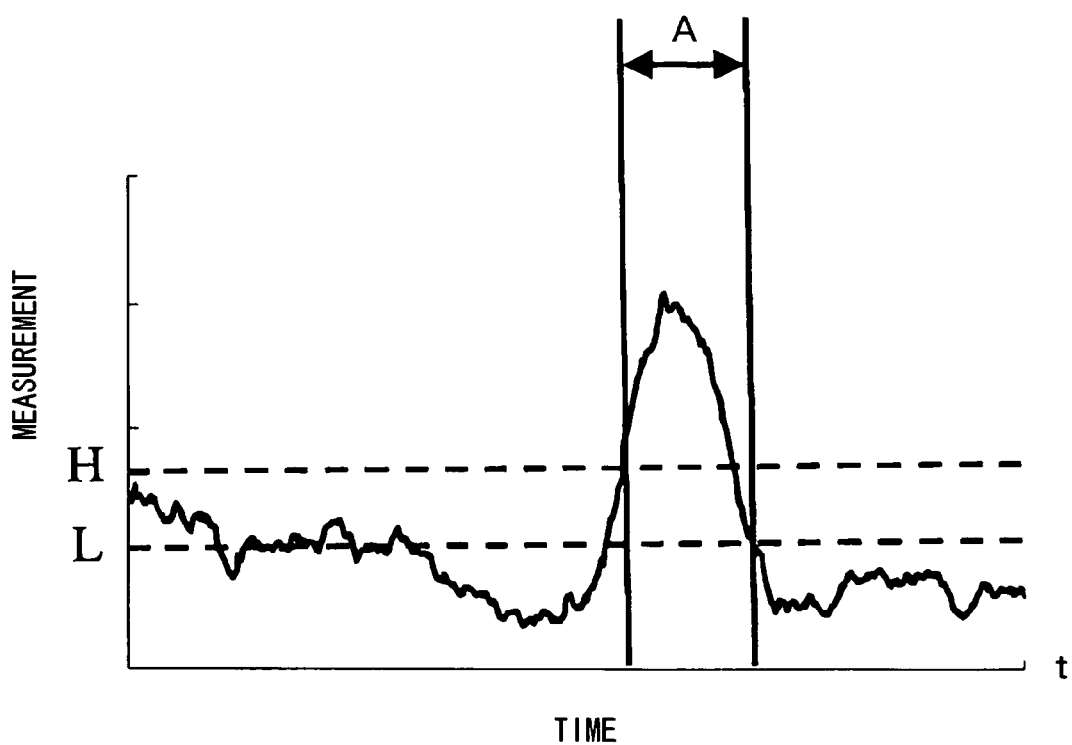
FIG. 6 is a waveform representing a period during which the peak is retrieved.

According to the procedure described, stored as the peak value is the maximum measurement during a peak retrieving period A including one peak, as seen in FIG. 6.

Figure 7:
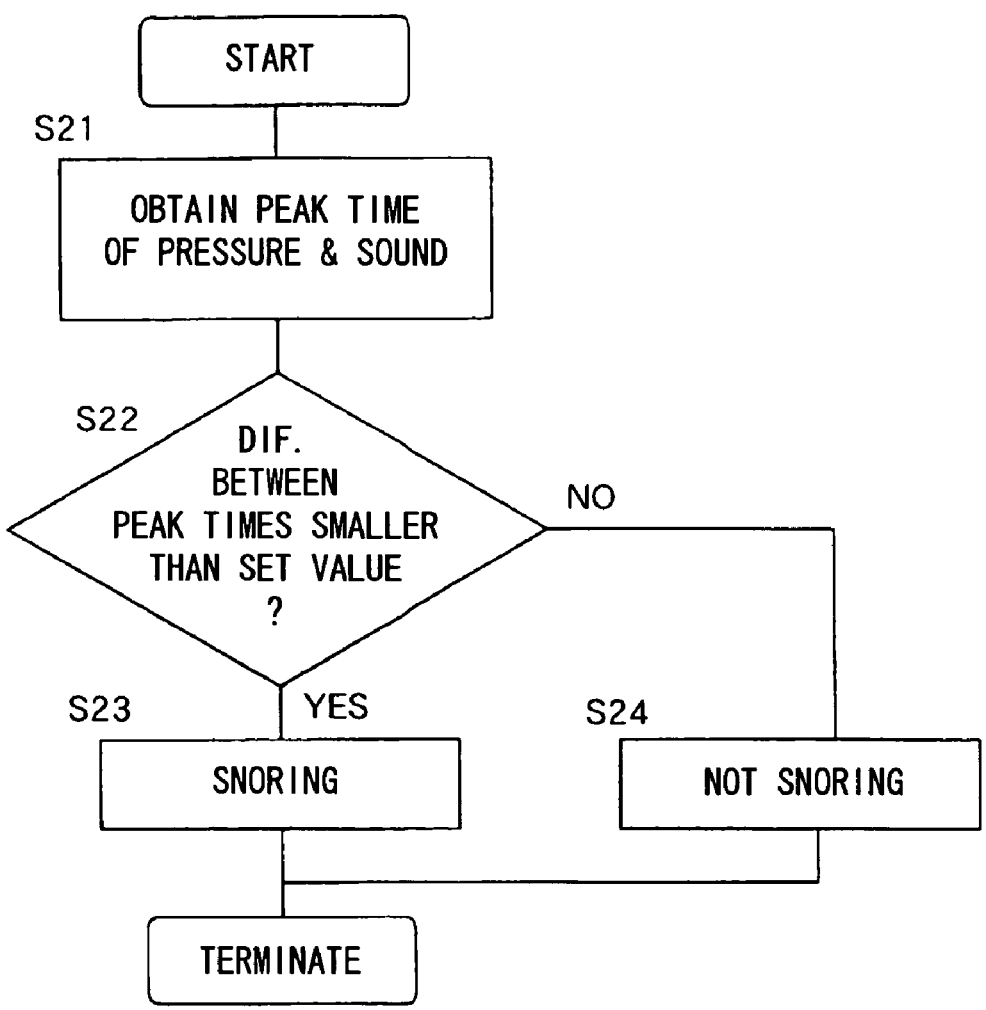
FIG. 7 is a flowchart showing a procedure of judging snoring.
Figure 8:
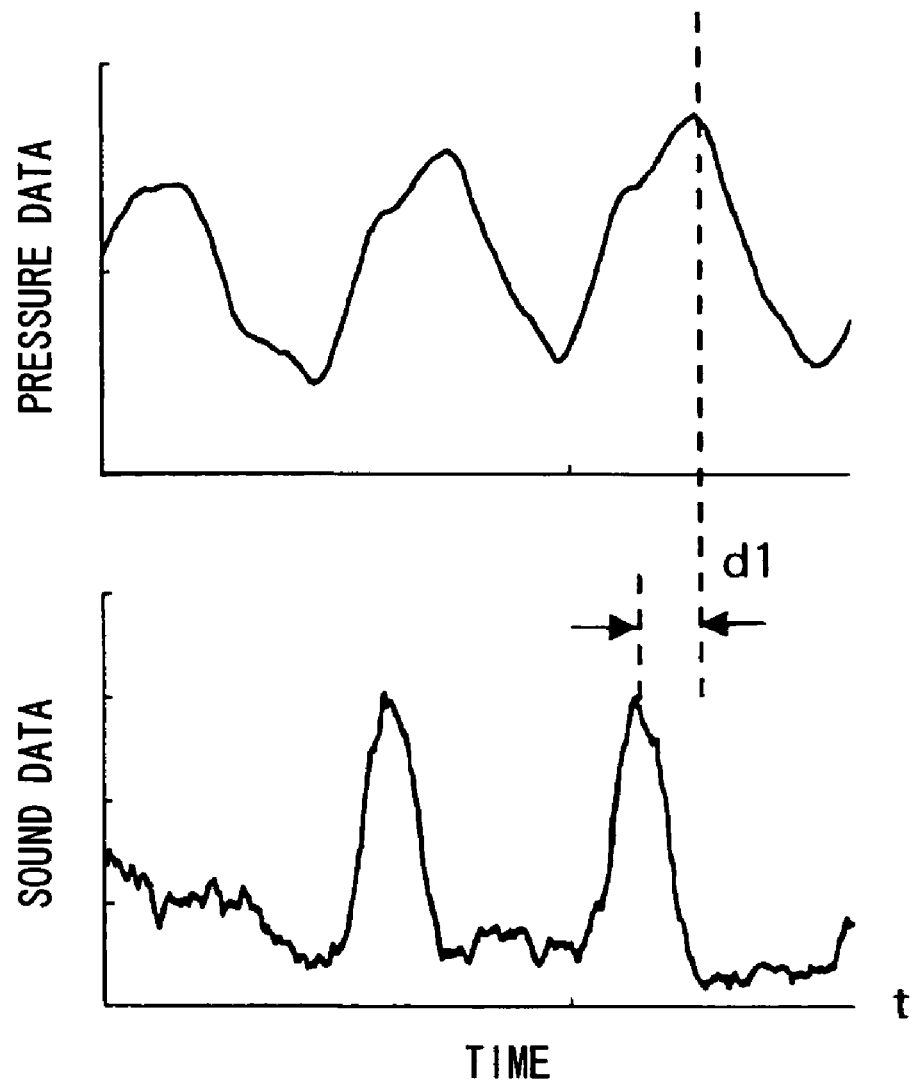
FIG. 8 is waveforms describing the difference between peak occurrence times.

FIG. 7 shows a specific procedure of judging the occurrence of snoring in the aforementioned step S5. First, step S21 obtains peak occurrence times, respectively, of pressure and sound generated continuously with time. In step S22 an inquiry is made as to whether the difference d1 between the peak occurrence time of pressure and the peak occurrence time of sound is smaller than a set value, as seen in FIG. 8. In this case settable as the set value is, for example, a suitable value corresponding to a sharpness of the peak of the waveform representing varying pressure data or sound data, e.g., 40% of the peak retrieving period shown in FIG. 6.

When the difference between the peak occurrence times is smaller than the set value in step S22 in FIG. 7, step S23 judges that snoring occurs. When the difference between the peak occurrence times is not smaller than the set value, step S24 does not judge that snoring occurs to terminate the procedure.

Figure 9:
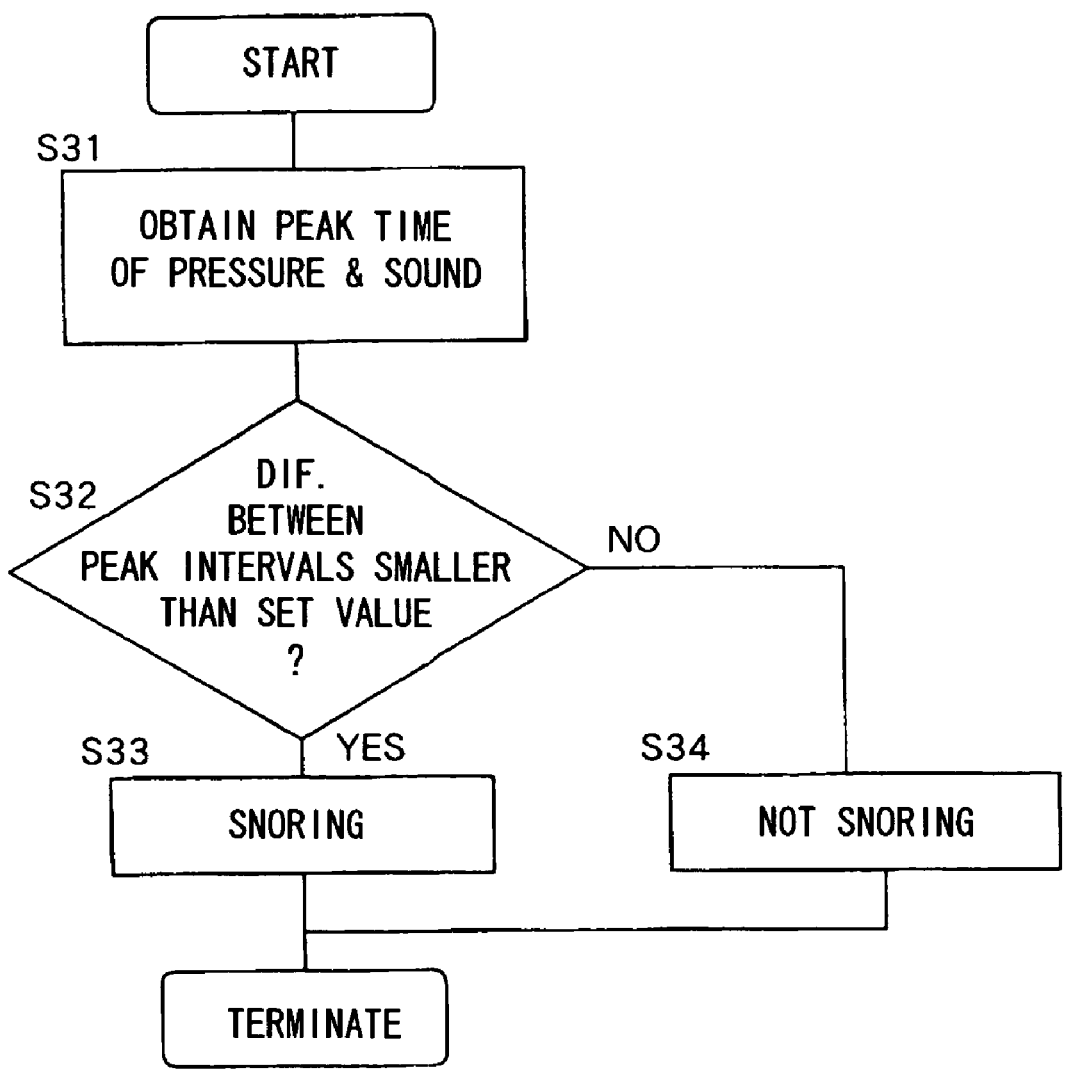
FIG. 9 is another flowchart showing a procedure of judging snoring.
Figure 10:
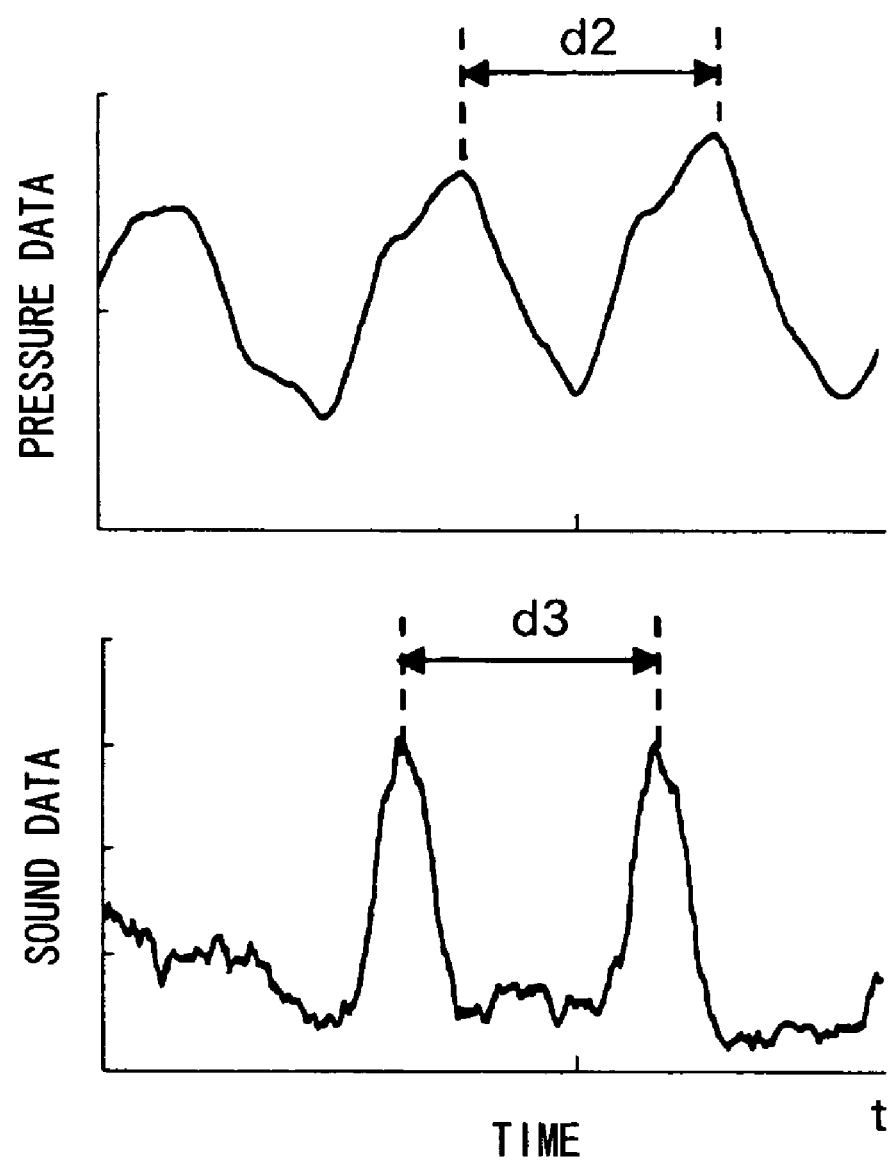
FIG. 10 is waveforms describing intervals of the peak occurrence times.

FIG. 9 shows another specific procedure of judging the occurrence of snoring. First, step S31 obtains peak occurrence times, respectively, of pressure and sound generated continuously with time, followed by step S32 to detect a peak interval d2 of pressure data and a peak interval d3 of sound data, judging whether the difference between the two intervals is smaller than a set value, as seen in FIG. 10. Incidentally settable as the set value is, for example, a suitable value corresponding to a sharpness of the peak of the waveform representing varying pressure data or sound data, e.g., 0.8 times the peak retrieving period shown in FIG. 6.

When the difference between the two peak intervals is smaller than the set value in step S32 in FIG. 9, step S33 judges that snoring occurs. When the difference between the two peak intervals is not smaller than the set value, step S34 does not judge that snoring occurs to terminate the procedure.

Figure 11:
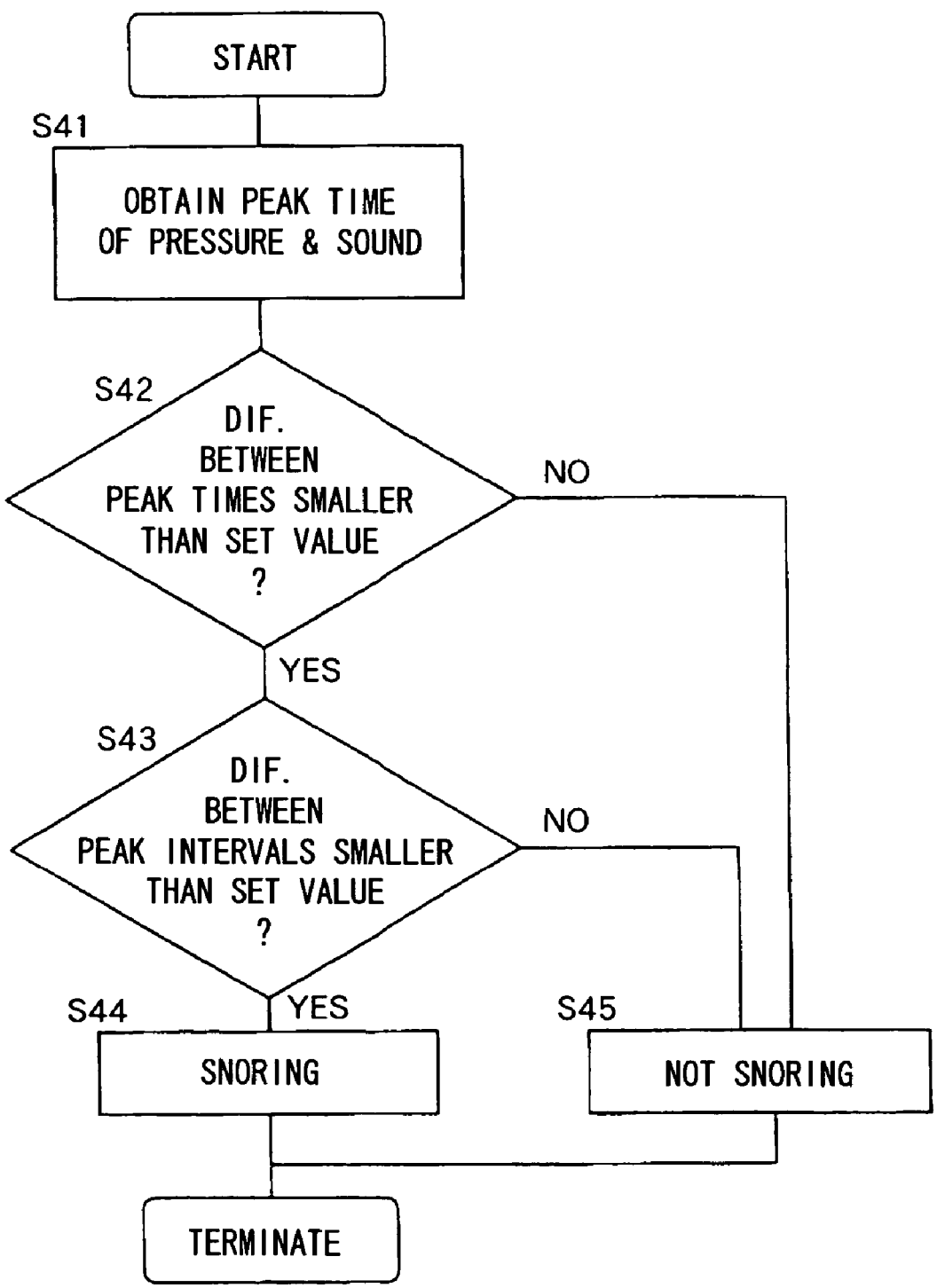
FIG. 11 is further another flowchart showing a procedure of judging snoring.
Figure 12:
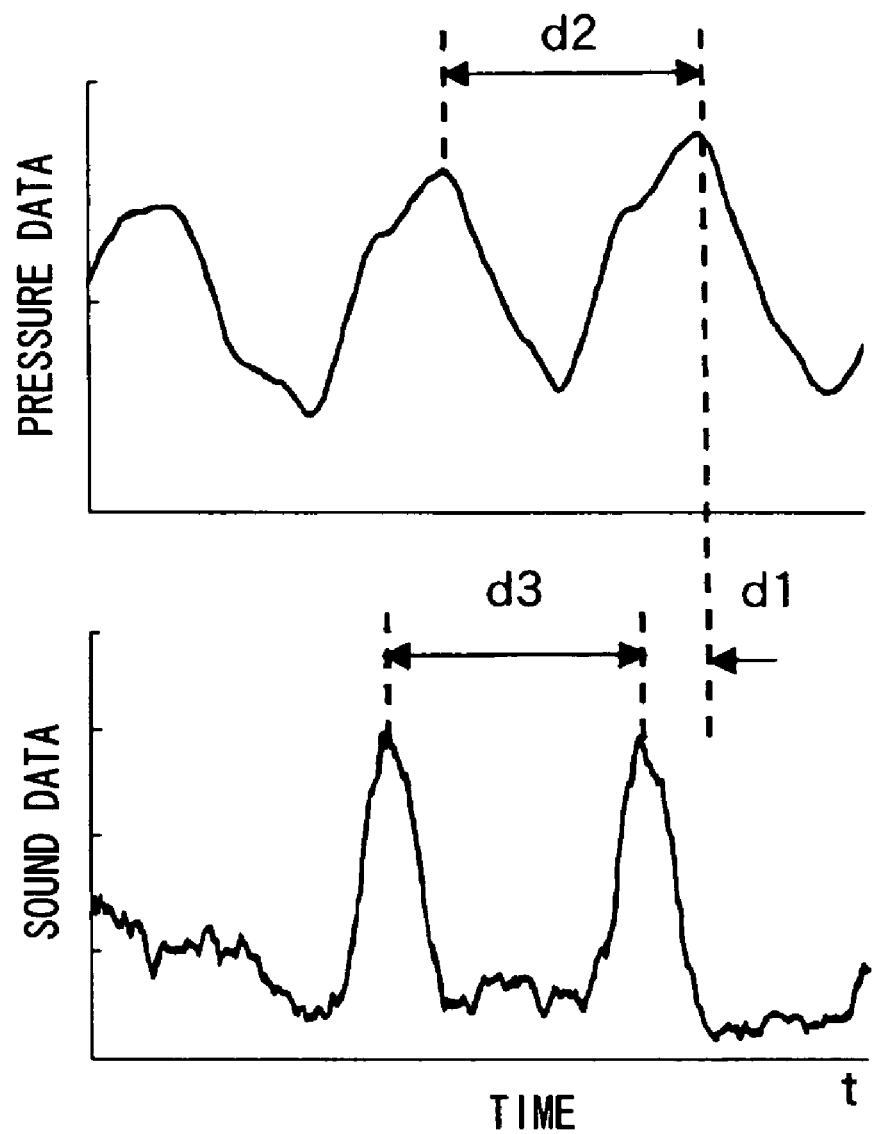
FIG. 12 is waveforms describing the difference between the peak occurrence times and the intervals of the peak occurrence times.
Figure 13:
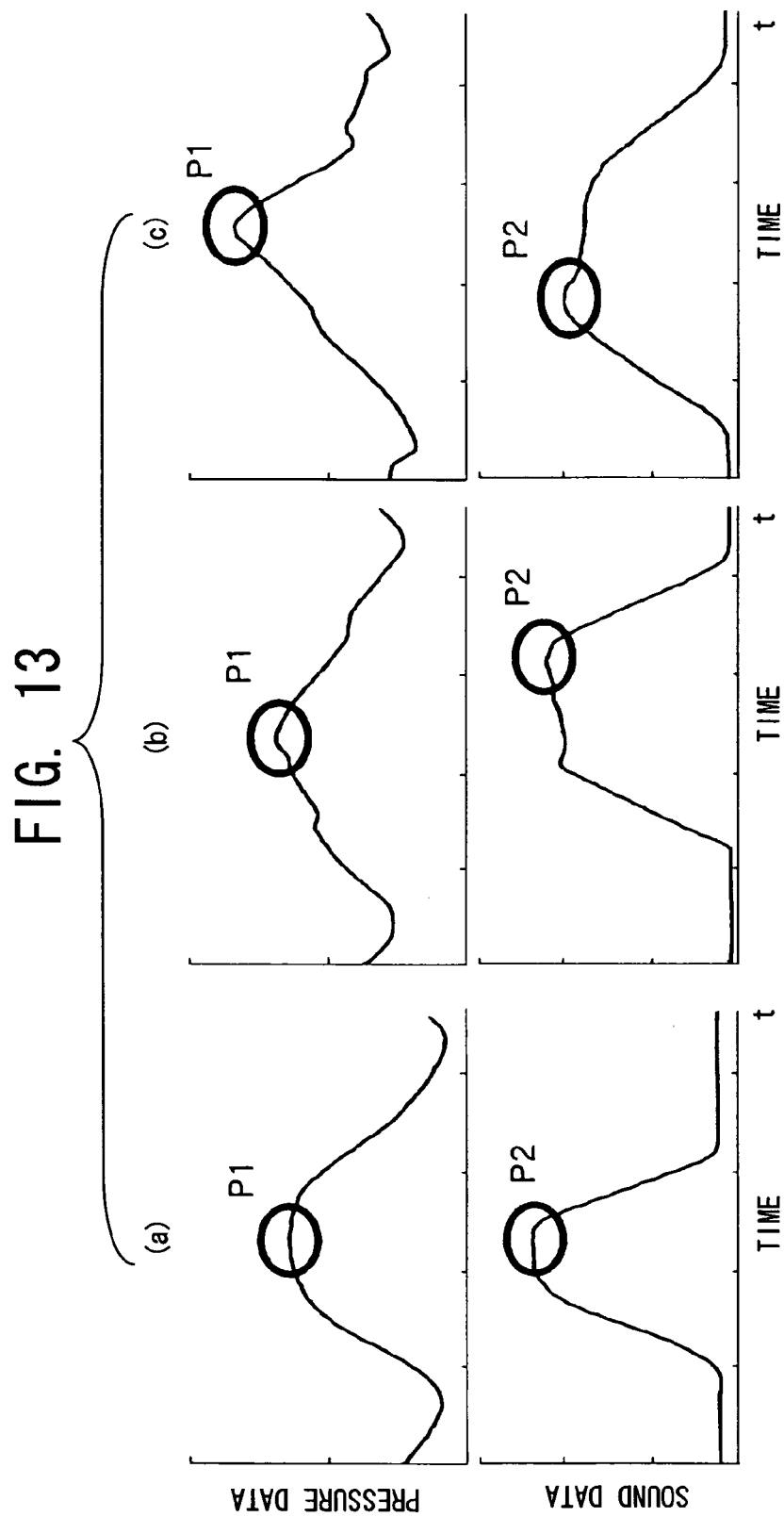
FIG. 13 is waveforms describing the difference of phase of the pressure data and sound data.

FIG. 11 shows further another specific procedure of judging the occurrence of snoring. First, step S41 obtains peak occurrence times, respectively, of pressure and sound generated continuously with time, followed by step S42 to judge whether the difference d1 between the two peak occurrence times is smaller than a set value, as seen in FIG. 12.

When the difference between the peak occurrence times is not smaller than the set value in step S42 in FIG. 11, step S45 does not judge that snoring occurs. On the other hand, if the difference between the peak occurrence times is smaller than the set value, step S43 follows to detect a peak interval d2 of pressure data and a peak interval d3 of sound data, judging whether the difference between the two intervals is smaller than a set value, as shown in FIG. 12.

If step S42 in FIG. 11 judges that the difference between the peak intervals is smaller than the set value, step S44 judges that snoring occurs. If step S42 does not judge that the difference between the peak intervals is smaller than the set value, step S45 does not judge that snoring occurs to terminate the procedure.

With the snore detection device embodying the present invention, the occurrence of snoring is judged in accordance with synchronous state of the two waveforms, i.e., the difference between the peak occurrence times, the difference between the peak occurrence intervals, or both the difference between the peak occurrence times and the difference between the peak occurrence intervals, based on the pressure data and the sound data obtained with respiration. This makes it possible to detect the occurrence of snoring with higher accuracy than conventionally.

Figure 14:
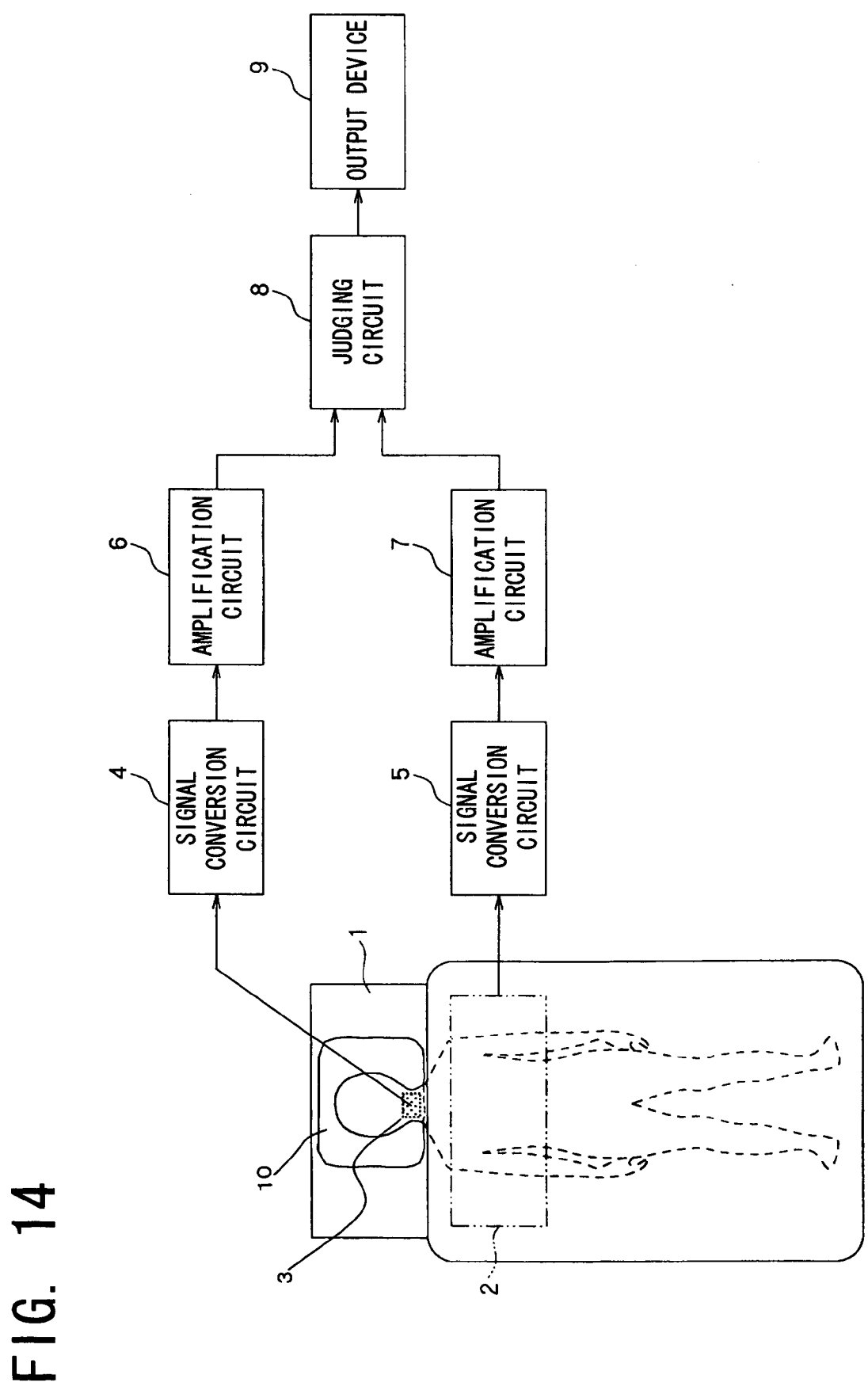
FIG. 14 is a block diagram showing another construction of a snore detection device according to the present invention.
Figure 15:
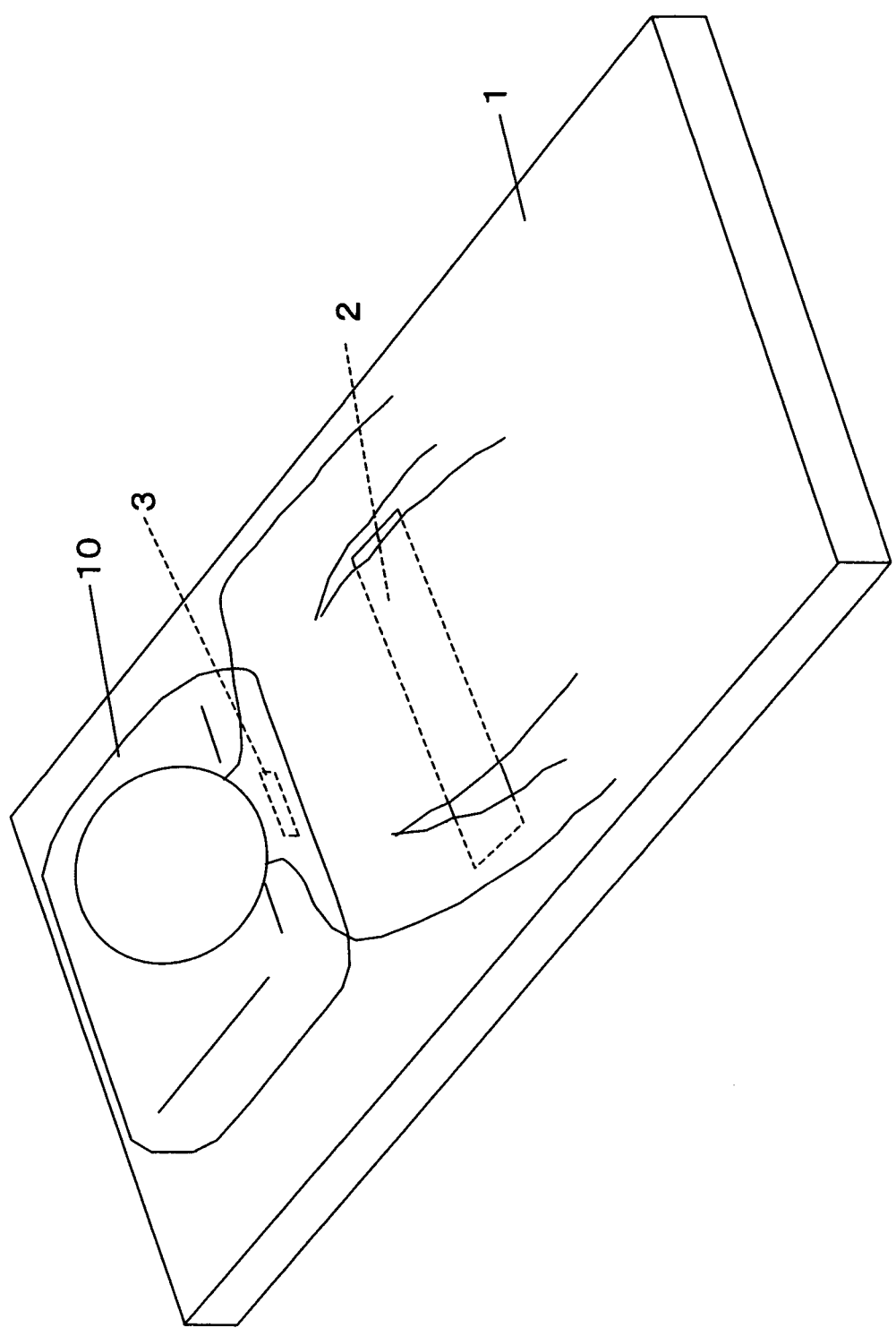
FIG. 15 is a diagram illustrating an arrangement of a pressure sensor and a sound sensor.
Figure 16:
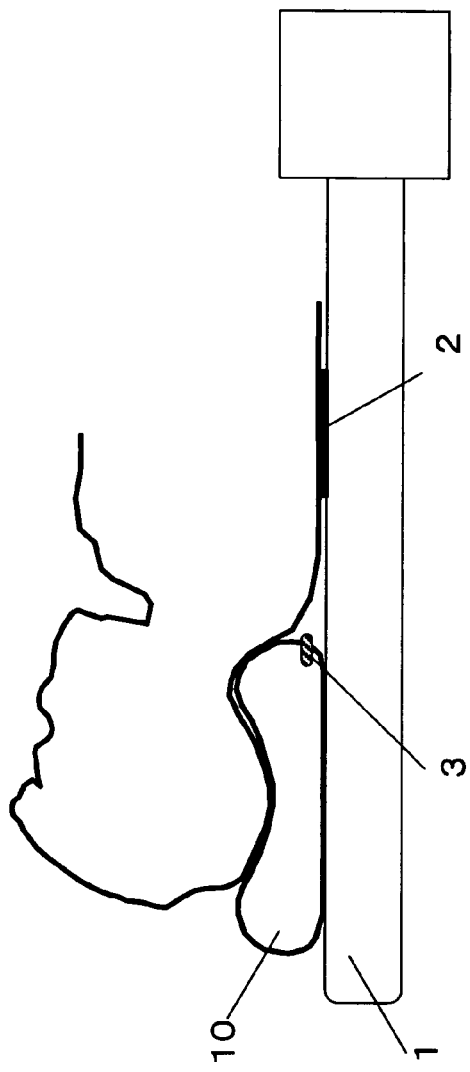
FIG. 16 is an illustration showing a specific position of the sound sensor.
Figure 17:
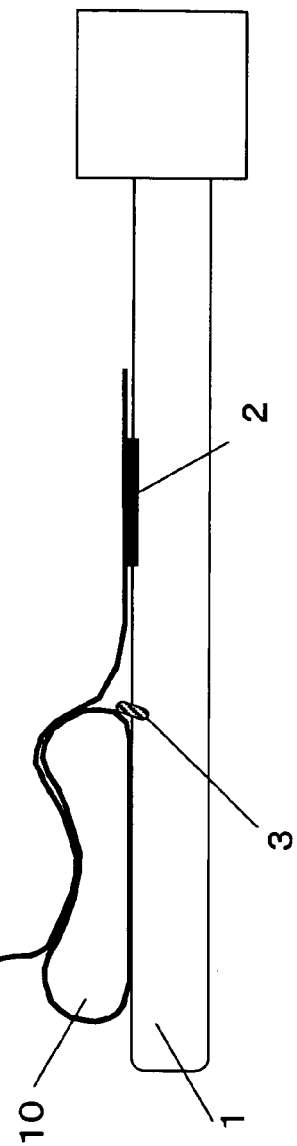
FIG. 17 is another illustration showing a specific position of the sound sensor.

Furthermore, according to another embodiment of the present invention, added to the snore detection device described is a pillow 10 for supporting a head of the sleeping human body, and a sound sensor 3 is attached to the pillow 10, as seen in FIG. 14. With reference to FIG. 15 and FIG. 16, the sound sensor 3 is installed so that the sound sensor 3 is positioned between a surface on which the pillow 10 is in contact with the mat 1 and a surface on which a head or a cervix of the human body is in contact with the pillow 10, approximately beneath the head or the cervix, and at a clearance created by following three; a curved surface from the cervix to a back of the human body, the pillow 10, and the mat 1.

The sound sensor 3 is further installed so that the sensor 3 is positioned on a surface of or inside the mat 1, beneath a head or a cervix, in the vicinity of a clearance created by following three: a curved surface from the cervix to a back of the human body, the pillow 10, and the mat 1, or a clearance created by a head, a curved face from a cervix to a back of the human body, and the mat 1 if the pillow 10 is not used.

The sound sensor 3 is thus installed on such a position as described above, to thereby place the sensor 3 closer to an upper respiratory tract, to reduce noise interference, whereby snoring sound generated by the human body can be detected with higher accuracy.

Furthermore, the sound sensor 3 is installed in the vicinity of the clearance created by a curved surface from the cervix to a back of the human body, the pillow 10, and the mat 1, or the clearance created by a head, a curved surface from a cervix to a back of the human body, and the mat 1 if the pillow 10 is not used, to thereby reduce a direct contact between the human body and the sound sensor 3, so that the user will not feel ill at ease, and the snoring sound can be detected accurately.

The device of the invention is not limited to the foregoing embodiments in construction but can be modified variously by one skilled in the art without departing from the spirit of the invention as set forth in the appended claims.

What is claimed is:

1. A snore detection device comprising a pressure sensor for detecting vibration generated by the human body with respiration, a sound sensor for detecting sound generated by the human body with respiration, and a judging circuit for judging whether snoring occurs based on output signals from the two sensors, the judging circuit comprising peak detection means for detecting a peak occurrence time in variations generated by the output signal of the pressure sensor and a peak occurrence time in variations generated by the output signal of the sound sensor, and judging means for judging whether snoring occurs based on the peak occurrence times, respectively, of vibration and sound detected by the peak detection means.

* * * * *